United States Patent
Katkevica et al.

(10) Patent No.: US 12,421,268 B2
(45) Date of Patent: Sep. 23, 2025

(54) PROCESS FOR PREPARING NUCLEOTIDE P(V) MONOMERS

(71) Applicant: Roche Innovation Center Copenhagen A/S, Horsholm (DK)

(72) Inventors: Dace Katkevica, Riga (LV); Martins Katkevics, Riga (LV); Erik Funder, Hillerod (DK); Nanna Albaek, Birkerod (DK)

(73) Assignee: Roche Innovation Center Copenhagen A/S, Horsholm (DK)

( * ) Notice: Subject to any disclaimer, the term of this patent is extended or adjusted under 35 U.S.C. 154(b) by 805 days.

(21) Appl. No.: 17/604,550

(22) PCT Filed: Apr. 14, 2020

(86) PCT No.: PCT/EP2020/060379
§ 371 (c)(1),
(2) Date: Oct. 18, 2021

(87) PCT Pub. No.: WO2020/212301
PCT Pub. Date: Oct. 22, 2020

(65) Prior Publication Data
US 2022/0194976 A1    Jun. 23, 2022

(30) Foreign Application Priority Data
Apr. 16, 2019    (EP) ..................... 19169409

(51) Int. Cl.
| | | |
|---|---|---|
| *C07H 1/02* | (2006.01) | |
| *C07H 21/00* | (2006.01) | |
| *C07H 19/06* | (2006.01) | |
| *C07H 19/16* | (2006.01) | |

(52) U.S. Cl.
CPC .............. *C07H 1/02* (2013.01); *C07H 21/00* (2013.01); *C07H 19/06* (2013.01); *C07H 19/16* (2013.01)

(58) Field of Classification Search
CPC .......... C07H 1/02; C07H 21/00; C07H 19/06; C07H 19/16
USPC ...................................... 536/26.71
See application file for complete search history.

(56) References Cited

U.S. PATENT DOCUMENTS

2022/0127301 A1    4/2022    Shimizu et al.

FOREIGN PATENT DOCUMENTS

| EP | 2620428 A1 | 7/2013 |
|---|---|---|
| JP | 2015-523316 A | 8/2015 |
| WO | 98/39352 A1 | 9/1998 |
| WO | 99/14226 A2 | 3/1999 |
| WO | 00/47599 A1 | 8/2000 |
| WO | 00/66604 A2 | 11/2000 |
| WO | 01/23613 A1 | 4/2001 |
| WO | 2004/046160 A2 | 6/2004 |
| WO | 2005/092909 A1 | 10/2005 |
| WO | 2007/090071 A2 | 8/2007 |
| WO | 2007/134181 A2 | 11/2007 |
| WO | 2008/150729 A2 | 12/2008 |
| WO | 2008/154401 A2 | 12/2008 |
| WO | 2009/006478 A2 | 1/2009 |
| WO | 2009/067647 A1 | 5/2009 |
| WO | 2010/036698 A1 | 4/2010 |
| WO | 2010/077578 A1 | 7/2010 |
| WO | 2011/005761 A1 | 1/2011 |
| WO | 2011/017521 A2 | 2/2011 |

(Continued)

OTHER PUBLICATIONS

Obika et al., Tetrahedron Letters, 1998, 39, 5401-5404.*

(Continued)

*Primary Examiner* — Ganapathy Krishnan
(74) *Attorney, Agent, or Firm* — Smith, Gambrell & Russell, LLP; Judy Jarecki-Black; Sharon Ngwenya

(57) ABSTRACT

The present invention relates to an optimized method for preparing a P(V) monomer of formula (IIIa) or (IIIb) from a nucleoside using DBU as a base at about 0.8 equivalent to nucleoside.

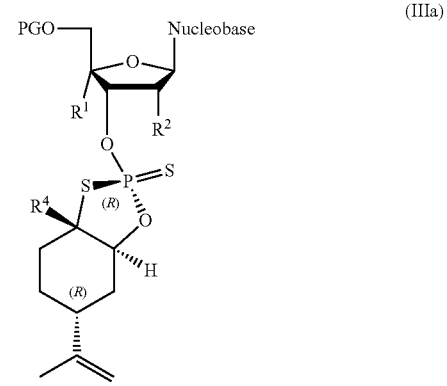

(IIIa)

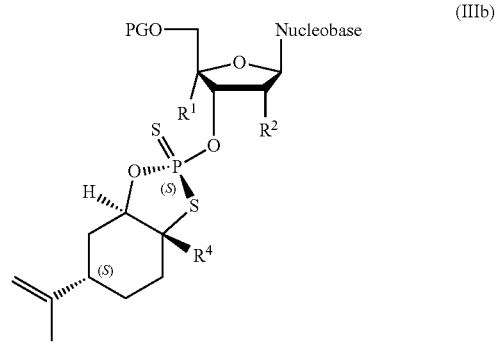

(IIIb)

14 Claims, No Drawings

(56) References Cited

FOREIGN PATENT DOCUMENTS

| WO | 2011/156202 A1 | 12/2011 | |
|---|---|---|---|
| WO | 2013/154798 A1 | 10/2013 | |
| WO | WO 2014/010250 A1 * | 1/2014 | ............... C07H 1/00 |
| WO | 2017/194498 A1 | 11/2017 | |
| WO | 2017/198775 A1 | 11/2017 | |
| WO | WO 2018/177825 A1 * | 10/2018 | ............... C07H 1/00 |
| WO | 2019/023459 A1 | 1/2019 | |
| WO | 2020/103929 A1 | 5/2020 | |
| WO | 2020/114495 A1 | 6/2020 | |

OTHER PUBLICATIONS

Knouse et al., Science, 2018, 361, 1234-1238.*
Bergstrom, D.E., "Unnatural nucleosides with unusual base pairing properties", Current Protocols in Nucleic Acid Chemistry, Suppl. 37 1.4.1 (2009).
Deleavey, G.F., et al., "Designing Chemically Modified Oligonucleotides for Targeted Gene Silencing", Chemistry and Biology, 19(8): 937-954 (2012).
Freier, S.M., et al., "The ups and downs of nucleic acid duplex stability: structure-stability studies on chemically-modified DNA:RNA duplexes", Nucl. Acid Res., 25(22): 4429-4443 (1997).
Hansen, L.D., et al., "Entropy titration. A calorimetric method for the determination of ?G°(K), ?H° and ?S°", Chem. Comm., 36-38 (1965).
Hirao, I., et al., "Natural versus Artificial Creation of Base Pairs in DNA: Origin of Nucleobases from the Perspectives of Unnatural Base Pair Studies", Accounts of Chemical Research, 45: 2055-2065 (2012).
Holdgate, G.A., et al., "Measurements of binding thermodynamics in drug discovery", Drug Discov. Today, 10(22): 1543-1550 (2005).
International Search Report and Written Opinion, received for PCT/EP2018/057069 on Jun. 22, 2018 (11 pages).
Knouse, K.W., et al., "Unlocking P(V): 1-18, Reagents for chiral phosphorothioate synthesis", Science, 361(6408): 1234-1238 (2018).
McTigue, P.M., et al., "Sequence-Dependent Thermodynamic Parameters for Locked Nucleic Acid (LNA)-DNA Duplex Formation", Biochemistry, 43(18): 5388-5405 (2004).
Mergny, J.L., et al., "Analysis of Thermal Melting Curves", Oligonucleotides, 13(6): 515-537 (2003).
Mitsuoka, Y., et al., "A bridged nucleic acid, 2',4'-BNA COC : synthesis of fully modified oligonucleotides bearing thymine, 5-methylcytosine, adenine and guanine 2',4'-BNA COC monomers and RNA-selective nucleic acid recognition", Nucleic Acids Research, 37(4): 1225-1238 (2009).
Morita, K., et al., "2'-O,4'-C-ethylene-bridged nucleic acids (ENA): highly nuclease-resistant and thermodynamically stable oligonucleotides for antisense drug", Bioorganic & Med.Chem. Lett., 12(1): 73-76 (2002).
Oka, N., et al., "Diastereocontrolled Synthesis of Dinucleoside Phosphorothioates Using a Novel Class of Activators, Dialkyl (cyanomethyl) ammonium Tetrafluoroborates", Journal of the American Chemical Society, 124(18): 4962-4963 (2002).
Oka, N., et al., "Solid-Phase Synthesis of Stereoregular Oligodeoxyribonucleoside Phosphorothioates Using Bicyclic Oxazaphospholidine Derivatives as Monomer Units", Journal of the American Chemical Society, 130(47): 16031-16037 (2008).
SantaLucia, J., "A unified view of polymer, dumbbell, and oligonucleotide DNA nearest-neighbor?thermodynamics", Proc. Natl. Acad. Sci. USA, 95: 1460-1465 (1998).
Seth, P.P., et al., "Synthesis and Biophysical Evaluation of 2',4'-Constrained 2'O-Methoxyethyl and 2',4'-Constrained 2'O-Ethyl Nucleic Acid Analogues", J. Org. Chem., 75(5): 1569-1581 (2010).
Sugimoto, N., et al., "Thermodynamic Parameters To Predict Stability of RNA/DNA Hybrid Duplexes", Biochemistry, 34: 11211-11216 (1995).
Uhlmann, E., "Recent advances in the medicinal chemistry of antisense oligonucleotides", Curr. Opinion in Drug Development, 3(2): 203-213 (2000).
Xu, D., et al., Enantiodivergent Formation of C—P Bonds: Synthesis of P-Chiral Phosphines and Methylphosphonate Oligonucleotides, Journal of the American Chemical Society, 142(12): 5785-5792 (2020).
Office Action received for Chinese Patent Application No. 2021-561622, mailed on Feb. 7, 2024, 9 pages (5 pages of English Translation and 4 pages of Original Document).

* cited by examiner

PROCESS FOR PREPARING NUCLEOTIDE P(V) MONOMERS

CROSS REFERENCE TO RELATED APPLICATIONS

This application is a national stage application, filed under 35 U.S.C. § 371, of International Patent Application No. PCT/EP2020/060379 filed on Apr. 14, 2020, which claims benefit of and priority to the European Patent Application 19169409.0 filed on Apr. 16, 2019, all of which are incorporated by reference in their entireties where permissible.

The invention relates to a novel process for preparing nucleotide P(V) monomers.

Nucleotide monomers are building blocks in the synthesis of oligonucleotides. Locked Nucleic Acid (LNA) oligonucleotides are synthetic oligonucleotides that are particularly useful as therapeutic synthetic antisense oligonucleotides. The use of LNA oligonucleotides as therapeutic agents has witnessed remarkable progress over recent decades leading to the development of molecules acting by diverse mechanisms including RNase H activating gapmers, splice switching oligonucleotides, microRNA inhibitors, siRNA or aptamers (S. T. Crooke, *Antisense drug technology: principles, strategies, and applications*, 2nd ed. ed., Boca Raton, FL: CRC Press, 2008). In this regard, phosphorothioate oligonucleotide meaning that at least some internucleoside linkages are phosphorothioates instead of the native phosphodiester have shown to be particularly pharmacologically interesting.

One of the consequences of using nucleotide monomers which are not chirally defined around phosphorous is that each phosphorothioate linkage is found as both the R and S stereoconfiguration (i.e. stereorandom phosphorothioate linkages). This results in that a particular phosphorothioate antisense oligonucleotide can contain many different diastereoisomers within the same sequence. For example, in the case of a phosphorothioate oligonucleotide of a given set sequence of 16 nucleotides in length, there are up to $2^{15}$ different diastereoisomers. This yields into potentially over 32,000 pharmacologically distinct compounds for the same set 16-oligonucleotide sequence. It is therefore highly desirable to identify, synthesize and/or isolate a pharmacologically optimal compound or a set of pharmacologically optimal compounds from such mixture. In fact, it can be reasonably presumed that such optimal compound(s) will have far greater therapeutic potential than the standard stereorandom phosphorothioate oligonucleotides.

One of the key steps in synthesizing such phosphorothioates oligonucleotides is the preparation of its building blocks, namely its monomers. This step can be suitably performed stereoselectively to direct the synthesis of antisense oligonucleotides to a preferred set of diastereoisomers or even to a single diastereoisomer.

Traditionally, the synthesis of monomers for phosphorothioates oligonucleotides has been performed with phosphorus/[P(III)]-based reagents systems. Recently Baran et al., Science, 2018, 361, 1234-1238 have offered a different approach using a phosphorus/[P(V)]-based reagents system, coined as a "platform for programmable, traceless, diastereoselectivephosphorus-sulfur incorporation". Baran et al. further propose that "the power of this reagent system is demonstrated through the robust and stereocontrolled synthesis of various nucleotidic architectures, including ASOs and CDNs, via an efficient, inexpensive, and operationally simple protocol."

Unfortunately, Baran et al. fail to describe the preparation of LNA nucleotide P(V) monomers of interest to the present inventors and only describe the preparation of DNA nucleotide P(V) monomers. After a thorough review of many parameters, reagents and process conditions, among many other recommendations, Baran et al. teach using 1,8-diazabicyclo[5.4.0]undec-7-ene (DBU) as base at 1.3 equivalent to nucleoside as the optimal conditions.

The inventors found a new process for preparing LNA nucleotide P(V) monomers through a P(V) reagent based system with surprisingly optimized conditions, resulting in a cheapest process with a relatively higher yield than described in the art.

SUMMARY OF THE INVENTION

In a first aspect, the invention relates to a method for preparing a P(V) monomer of formula (IIIa) or (IIIb):

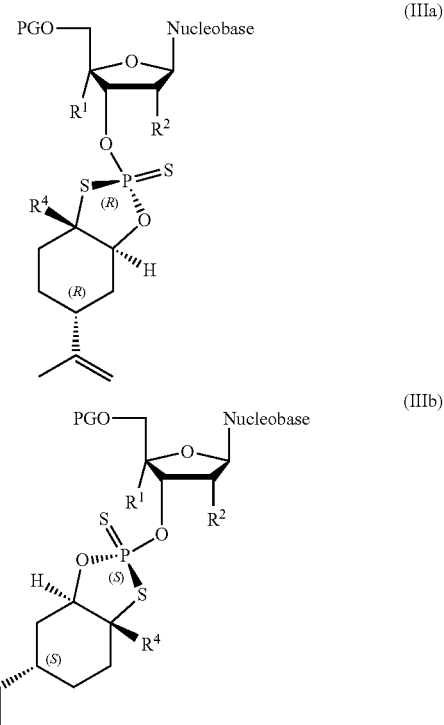

starting from a nucleoside using 1,8-diazabicyclo[5.4.0] undec-7-ene (DBU) as base, wherein DBU is used in an amount of about 0.8 equivalent to nucleoside.

In a second aspect the invention relates to a compound of formula (IIIa) or (IIIb):

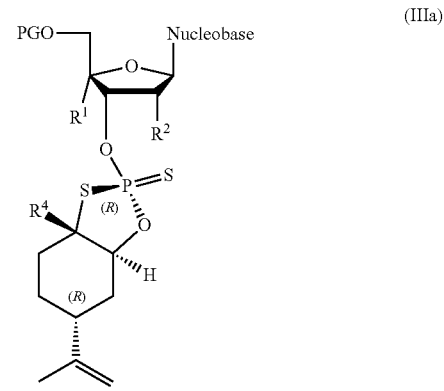

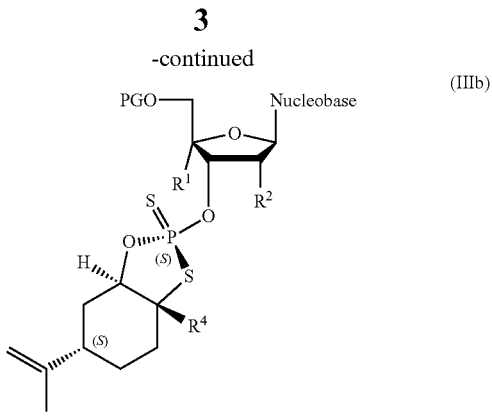

(IIIb)

wherein R¹, R², R³ and R⁴ are as defined herein.

In a third aspect, the invention relates to a compound of formula (IIIa) or (IIIb) as prepared according to the process of the invention.

In a fourth aspect, the invention relates to an LNA oligonucleotide manufactured according to a method of the invention.

Other aspects of the invention will be described more in details hereinbelow.

Definitions

The term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and propyl.

The term "amino", alone or in combination, signifies the primary amino group (—$NH_2$), the secondary amino group (—NH—), or the tertiary amino group (—N—).

The term "amino protecting group" denotes a protecting group of the amino group. Amines are functional groups that often require protecting groups during organic reactions. Carbamates such as t-butoxycarbonyl (Boc, e.g. removed by concentrated strong acid (such as HCl or CF3COOH), or by heating to >80° C.), benzyloxycarbonyl (Cbz, e.g. removed by hydrogenolysis), or 9-fluorenylmethoxycarbonyl (Fmoc e.g. removed by base, such as piperidine) are commonly used amine protecting groups. Additional options for protecting groups with different deprotection conditions can be used, such as described by Peter Wipf, University of Pittsburgh, Pa., USA, and colleagues who have developed a useful protecting group for primary, secondary, and heterocyclic amines: 2,2,6,6-tetramethylpiperidin-1-yloxycarbonyl (Tempoc). Acetyl (Ac) group is common in oligonucleotide synthesis for protection of N4 in cytosine and N6 in adenine nucleic bases and can be removed by treatment with a base, most often, with aqueous or gaseous ammonia or methylamine. Ac is too stable to be readily removed from aliphatic amides. Benzoyl (Bz) group is also common in oligonucleotide synthesis for protection of N4 in cytosine and N6 in adenine nucleic bases and is removed by treatment with a base, most often with aqueous or gaseous ammonia or methylamine. Bz is too stable to be readily removed from aliphatic amides. Other suitable amino protecting groups commonly use d can also be considered by the person skilled in the art such as DMF or iBu.

The term "aryl", alone or in combination, denotes a monovalent aromatic carbocyclic mono- or bicyclic ring system comprising 6 to 10 carbon ring atoms, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of aryl include phenyl and naphthyl, in particular phenyl.

The expression "in an amount of about 0.8 equivalent to nucleoside" when referring to DBU means a range of from 0.7 to 0.9 of equivalent to nucleoside. In this context, equivalent means molar equivalent. In other words, it denotes an about 0.7 to 0.9 DBU:1 nucleoside molar ratio.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The terms "hydroxyl" and "hydroxy", alone or in combination, signify the —OH group.

"Hydroxyl protecting group" is a protecting group of the hydroxyl group and is also used to protect thiol groups. Examples of hydroxyl protecting groups are acetyl (Ac), benzoyl (Bz), benzyl (Bn), β-methoxyethoxymethyl ether (MEM), dimethoxytrityl (or bis-(4-methoxyphenyl)phenylmethyl) (DMT), trimethoxytrityl (or tris-(4-methoxyphenyl) phenylmethyl) (TMT), methoxymethyl ether (MOM), methoxytrityl [(4-methoxyphenyl)diphenylmethyl (MMT), p-methoxybenzyl ether (PMB), methylthiomethyl ether, pivaloyl (Piv), tetrahydropyranyl (THP), tetrahydrofuran (THF), trityl or triphenylmethyl (Tr), silyl ether (for example trimethylsilyl (TMS), tert-butyldimethylsilyl (TBDMS), triiso-propylsilyloxymethyl (TOM) and triisopropylsilyl (TIPS) ethers), methyl ethers and ethoxyethyl ethers (EE). Particular examples of hydroxyl protecting group are DMT and TMT, in particular DMT.

The term "LNA monomer" refers to an LNA nucleotide, meaning a nucleotide for which the nucleoside is an LNA nucleoside as defined herein.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins.

The oligonucleotide of the invention can also be present in the form of zwitterions. Particularly preferred pharmaceutically acceptable salts of the invention are the sodium, lithium, potassium and trialkylammonium salts.

The term "protecting group", alone or in combination, signifies a group which selectively blocks a reactive site in a multifinctional compound such that a chemical reaction can be carried out selectively at another unprotected reactive site. Protecting groups can be removed. Exemplary protecting groups are amino-protecting groups, carboxy-protecting groups or hydroxy-protecting groups.

"Phosphate protecting group" is a protecting group of the phosphate group. Examples of phosphate protecting group are 2-cyanoethyl and methyl. A particular example of phosphate protecting group is 2-cyanoethyl.

If one of the starting materials or compounds of the invention contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self complementarity is less than 50% across of the full length of the oligonucleotide Contiguous Nucleotide Sequence The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence, such as a F-G-F' gapmer region, and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Nucleobase

The term nucleobase includes the purine (e.g. adenine and guanine) and pyrimidine (e.g. uracil, thymine and cytosine) moieties present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Stereodefined Oligonucleotide

A stereodefined oligonucleotide is an oligonucleotide wherein at least one of the internucleoside linkages is a stereodefined internucleoside linkage.

A stereodefined phosphorothioate oligonucleotide is an oligonucleotide wherein at least one of the internucleoside linkages is a stereodefined phosphorothioate internucleoside linkage.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the proportion of nucleotides in a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences (when aligned with the target sequence 5'-3' and the oligonucleotide sequence from 3'-5'), dividing by the total number of nucleotides in the oligonucleotide and multiplying by 100. In such a comparison a nucleobase/nucleotide which does not align (form a base pair) is termed a mismatch. Preferably, insertions and deletions are not allowed in the calculation of % complementarity of a contiguous nucleotide sequence.

The term "fully complementary", refers to 100% complementarity.

Identity

The term "Identity" as used herein, refers to the number of nucleotides in percent of a contiguous nucleotide sequence in a nucleic acid molecule (e.g. oligonucleotide) which, at a given position, are identical to (i.e. in their ability to form Watson Crick base pairs with the complementary nucleoside) a contiguous nucleotide sequence, at a given position of a separate nucleic acid molecule (e.g. the target nucleic acid). The percentage is calculated by counting the number of aligned bases that are identical between the two sequences dividing by the total number of nucleotides in the oligonucleotide and multiplying by 100. Percent Identity= (Matches×100)/Length of aligned region. Preferably, insertions and deletions are not allowed in the calculation of % complementarity of a contiguous nucleotide sequence.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy $\Delta G°$ is a more accurate representation of binding affinity and is related to the dissociation constant ($K_d$) of the reaction by $\Delta G°=-RT \ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for $\Delta G°$ measurements. $\Delta G°$ can also be estimated numerically by using the nearest neighbor model as described by SantaLucia, 1998, *Proc Natl Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated $\Delta G°$ values below −10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated $\Delta G°$ value of −10 to −60 kcal, such as −12 to −40, such as from −15 to −30 kcal or −16 to −27 kcal such as −18 to −25 kcal.

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradical bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO 2011/017521) or tricyclic nucleic acids (WO 2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides.

A 2' sugar modified nucleoside is a nucleoside which has a substituent other than H or —OH at the 2' position (2' substituted nucleoside) or comprises a 2' linked biradical capable of forming a bridge between the 2' carbon and a second carbon in the ribose ring, such as LNA (2'-4' biradical bridged) nucleosides.

Indeed, much focus has been spent on developing 2' modified nucleosides, and numerous 2' modified nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-fluoro-RNA and 2'-F-ANA nucleoside. Further examples can be found in e.g. Freier & Altmann; Nucl. Acid Res., 1997, 25, 4429-4443 and Uhlmann; Curr. Opinion in Drug Development, 2000, 3(2), 293-213 and Deleavey and Damha, Chemistry and Biology 2012, 19, 937. Below are illustrations of some 2' substituted modified nucleosides.

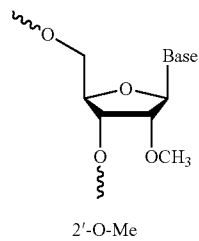

2'-O-Me

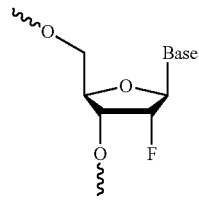

2'-F-RNA

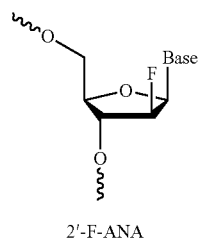

2'-F-ANA

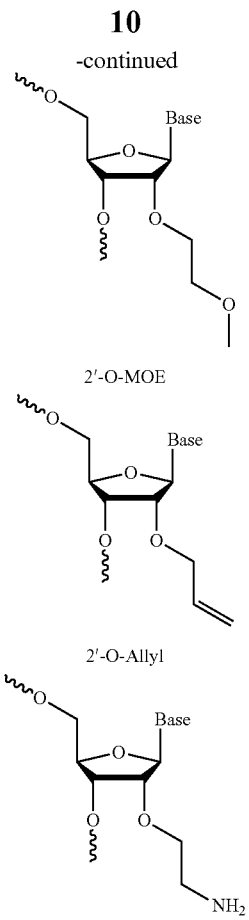

2'-O-MOE

2'-O-Allyl

2'-O-Ethylamine

In relation to the present invention 2' modified does not include 2' bridged molecules like LNA.

Locked Nucleic Acid Nucleosides (LNA Nucleosides)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81 and Mitsuoka et al., Nucleic Acids Research 2009, 37(4), 1225-1238.

The 2'-4' bridge comprises 2 to 4 bridging atoms and is in particular of formula —X—Y—, Y being linked to C4' and X linked to C2', wherein X is oxygen, sulfur, —CR$^a$R$^b$—, —C(R$^a$)=C(R$^b$)—, —C(=CR$^a$R$^b$)—, —C(R$^a$)=N—, —Si(R$^a$)$_2$—, —SO$_2$—, —NR$^a$—; —O—NR$^a$—, —NR$^a$—O—, —C(=J)-, Se, —O—NR$^a$—, —NR$^a$—CR$^a$R$^b$—, —N(R$^a$)—O— or —O—CR$^a$R$^b$—;

Y is oxygen, sulfur, —(CR$^a$R$^b$)$_n$—, —CR$^a$R$^b$—O—CR$^a$R$^b$—, —C(R$^a$)=C(R$^b$)—, —C(R$^a$)=N—, —Si(R$^a$)$_2$—, —SO$_2$—, —NR$^a$—, —C(=J)-, Se, —O—NR$^a$—, —NR$^a$—CR$^a$R$^b$—, —N(R$^a$)—O— or —O—CR$^a$R$^b$—.

with the proviso that —X—Y— is not —O—O—, Si(R$^a$)$_2$—Si(R$^a$)$_2$—, —SO$_2$—SO$_2$—, —C(R$^a$)=C(R$^b$)—C(R$^a$)=C(R$^b$), —C(R$^a$)=N—C(R$^a$)=N—, —C(R$^a$)=N—C(R$^a$)=C(R$^b$), —C(R$^a$)=C(R$^b$)—C(R$^a$)=N— or —Se—Se—;

J is oxygen, sulfur, =CH$_2$ or =N(R$^a$);

R$^a$ and R$^b$ are independently selected from hydrogen, halogen, hydroxyl, cyano, thiohydroxyl, alkyl, substituted alkyl, alkenyl, substituted alkenyl, alkynyl, substituted alkynyl, alkoxy, substituted alkoxy, alkoxyalkyl, alkenyloxy, carboxyl, alkoxycarbonyl, alkylcarbonyl, formyl, aryl, heterocyclyl, amino, alkylamino, carbamoyl, alkylaminocarbonyl, aminoalkylaminocarbonyl, alkylaminoalkylaminocarbonyl, alkylcarbonylamino, carbamido, alkanoyloxy, sulfonyl, alkylsulfonyloxy, nitro, azido, thiohydroxylsulfidealkylsulfanyl, aryloxycarbonyl, aryloxy, arylcarbonyl, heteroaryl, heteroaryloxycarbonyl, heteroaryloxy, heteroarylcarbonyl, —OC(=X$^a$)R$^c$, —OC(=X$^a$)NR$^c$R$^d$ and —NR$^c$C(=X$^a$)NR$^c$R$^d$;

or two geminal R$^a$ and R$^b$ together form optionally substituted methylene;

or two geminal R$^a$ and R$^b$, together with the carbon atom to which they are attached, form cycloalkyl or halocycloalkyl, with only one carbon atom of —X—Y—;

wherein substituted alkyl, substituted alkenyl, substituted alkynyl, substituted alkoxy and substituted methylene are alkyl, alkenyl, alkynyl and methylene substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl, formyl, heterocyclyl, aryl and heteroaryl;

X$^a$ is oxygen, sulfur or —NR$^c$;

R$^c$, R$^d$ and R$^e$ are independently selected from hydrogen and alkyl; and n is 1, 2 or 3.

In a further particular embodiment of the invention, X is oxygen, sulfur, —NR$^a$—, —CR$^a$R$^b$— or —C(=CR$^a$R$^b$)—, particularly oxygen, sulfur, —NH—, —CH$_2$— or —C(=CH$_2$)—, more particularly oxygen.

In another particular embodiment of the invention, Y is —CR$^a$R$^b$—, —CR$^a$R$^b$—CR$^a$R$^b$— or —CR$^a$R$^b$—CR$^a$R$^b$—CR$^a$R$^b$—, particularly —CH$_2$—CHCH$_3$—, —CHCH$_3$—CH$_2$—, —CH$_2$—CH$_2$— or —CH$_2$—CH$_2$—CH$_2$—.

In a particular embodiment of the invention, —X—Y— is —O-(CR$^a$R$^b$)$_n$—, —S—CR$^a$R$^b$—, —N(R$^a$)CR$^a$R$^b$—, —CR$^a$R$^b$—CR$^a$R$^b$—, —O—CR$^a$R$^b$—O—CR$^a$R$^b$—, —CR$^a$R$^b$—O—CR$^a$R$^b$—, —C(=CR$^a$R$^b$)—CR$^a$R$^b$—, —N(R$^a$)CR$^a$R$^b$—, —O—N(R$^a$)—CR$^a$R$^b$— or —N(R$^a$)—O—CR$^a$R$^b$—.

In a particular embodiment of the invention, R$^a$ and R$^b$ are independently selected from the group consisting of hydrogen, halogen, hydroxyl, alkyl and alkoxyalkyl, in particular hydrogen, halogen, alkyl and alkoxyalkyl.

In another embodiment of the invention, R$^a$ and R$^b$ are independently selected from the group consisting of hydrogen, fluoro, hydroxyl, methyl and —CH$_2$—O—CH$_3$, in particular hydrogen, fluoro, methyl and —CH$_2$—O—CH$_3$.

Advantageously, one of R$^a$ and R$^b$ of —X—Y— is as defined above and the other ones are all hydrogen at the same time.

In a further particular embodiment of the invention, R$^a$ is hydrogen or alkyl, in particular hydrogen or methyl.

In another particular embodiment of the invention, R$^b$ is hydrogen or alkyl, in particular hydrogen or methyl.

In a particular embodiment of the invention, one or both of R$^a$ and R$^b$ are hydrogen.

In a particular embodiment of the invention, only one of R$^a$ and R$^b$ is hydrogen.

In one particular embodiment of the invention, one of R$^a$ and R$^b$ is methyl and the other one is hydrogen.

In a particular embodiment of the invention, R$^a$ and R$^b$ are both methyl at the same time.

In a particular embodiment of the invention, —X—Y- is —O—CH$_2$—, —S—CH$_2$—, —S—CH(CH$_3$)—, —NH—CH$_2$—, —O—CH$_2$CH$_2$—, —O—CH(CH$_2$—O—CH$_3$)—, —O—CH(CH$_2$CH$_3$)—, —O—CH(CH$_3$)—, —O—CH$_2$—O—CH$_2$—, —O—CH$_2$—O—CH$_2$—, —CH$_2$—O—CH$_2$—, —C(=CH$_2$)CH$_2$—, —C(=CH$_2$)CH(CH$_3$)—, —N(OCH$_3$)CH$_2$— or —N(CH$_3$)CH$_2$—;

In a particular embodiment of the invention, —X—Y— is —O—CR$^a$R$^b$— wherein R$^a$ and R$^b$ are independently selected from the group consisting of hydrogen, alkyl and alkoxyalkyl, in particular hydrogen, methyl and —CH$_2$—O—CH$_3$.

In a particular embodiment, —X—Y— is —O—CH$_2$— or —O—CH(CH$_3$)—, particularly —O—CH$_2$—.

The 2'-4' bridge may be positioned either below the plane of the ribose ring (beta-D-configuration), or above the plane of the ring (alpha-L-configuration), as illustrated in formula (A) and formula (B) respectively.

It will be recognized than, unless specified, the LNA nucleosides may be in the beta-D or alpha-L stereoisoform.

Particular examples of LNA nucleosides of the invention are presented in Scheme 1 (wherein B is as defined above).

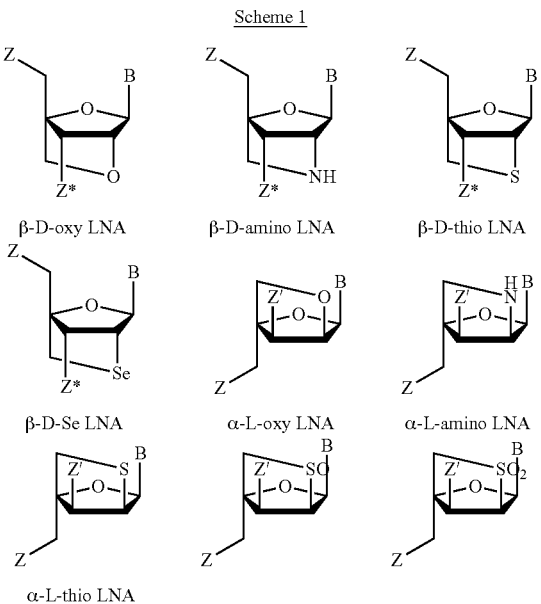

Scheme 1

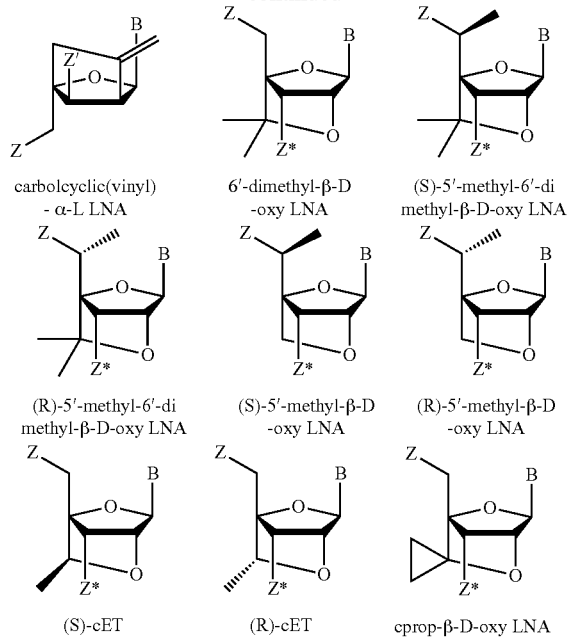
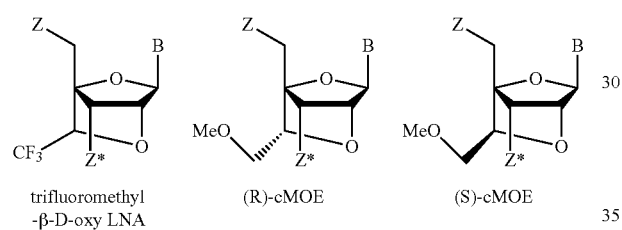
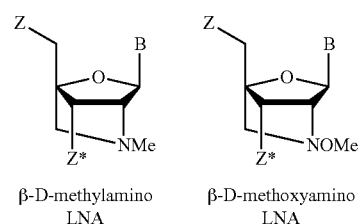
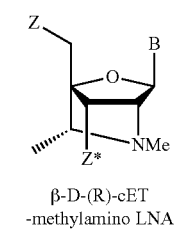
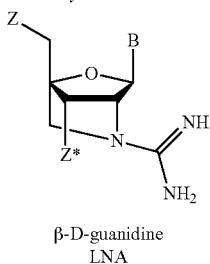
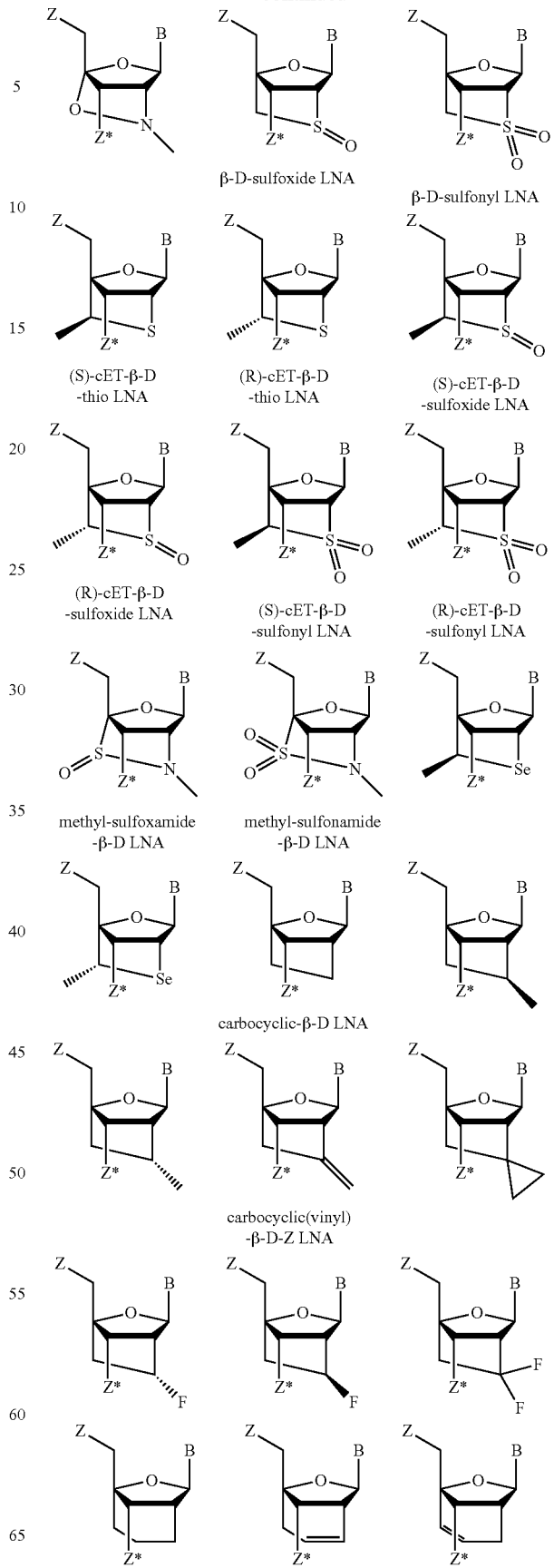

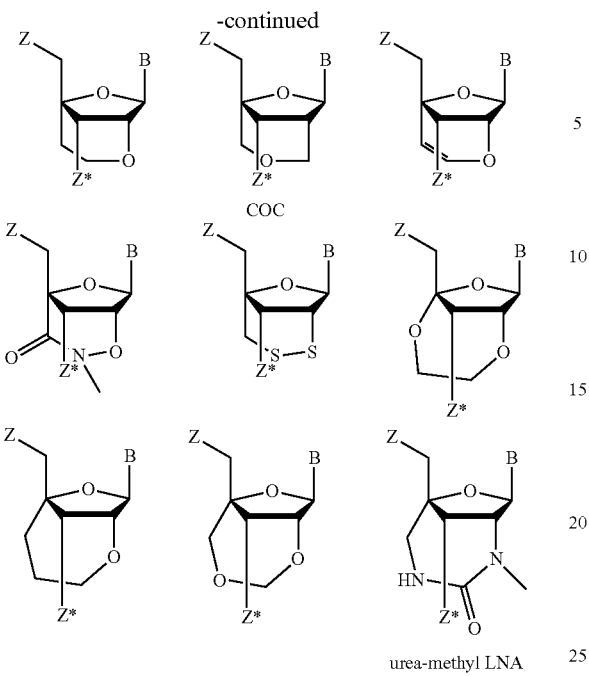

urea-methyl LNA

Particular LNA nucleosides are beta-D-oxy-LNA, 6'-methyl-beta-D-oxy LNA such as (S)-6'-methyl-beta-D-oxy-LNA ((S)-cET) and ENA.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH, Lucerne, Switzerland.

DETAILED DESCRIPTION OF THE INVENTION

In one aspect, the invention relates to a method for preparing a P(V) monomer of formula (IIIa) or (IIIb) comprising the step of reacting a modified nucleoside of formula (I):

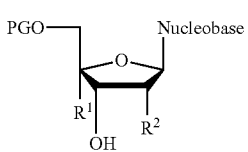

(I)

wherein PG is a hydroxyl protecting group,
$R^1$ is H and $R^2$ is —O(CH$_2$)$_2$OCH$_3$ or,
$R^1$ and $R^2$ together form a 2'-4' bridge selected from —CH$_2$—O— or —CH(CH$_3$)O—, wherein the oxygen is attached via position $R^2$;
with a compound of formula (IIa) or (IIb):

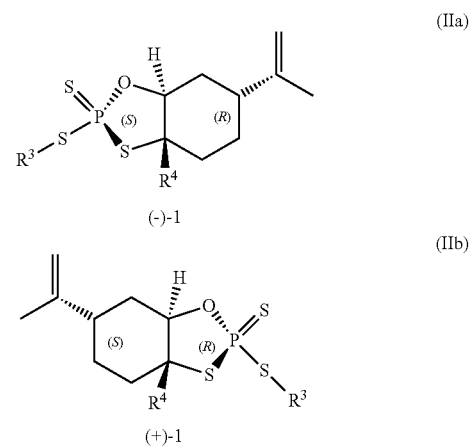

(IIa)

(-)-1

(IIb)

(+)-1 wherein $R^3$ is a $C_6$-$C_{10}$ aryl substituted by halo and halo is selected from F, Cl and Br and $R^4$ is a linear or branched $C_1$-$C_6$-alkyl;
with 1,8-diazabicyclo[5.4.0]undec-7-ene (DBU) as base, wherein DBU is used in an amount of about 0.8 equivalent to nucleoside of formula (I);
to produce a monomer of formula (IIIa) or (IIIb):

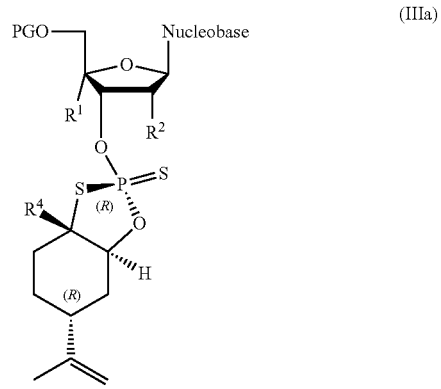

(IIIa)

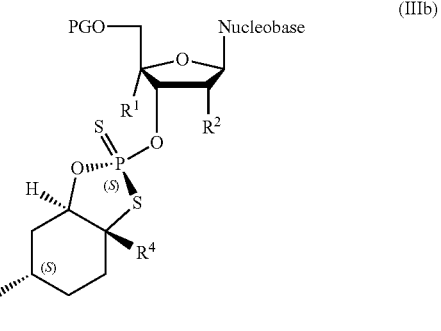

(IIIb)

In one or all embodiments of the invention, the compound of formula (IIa) or (IIb) is:

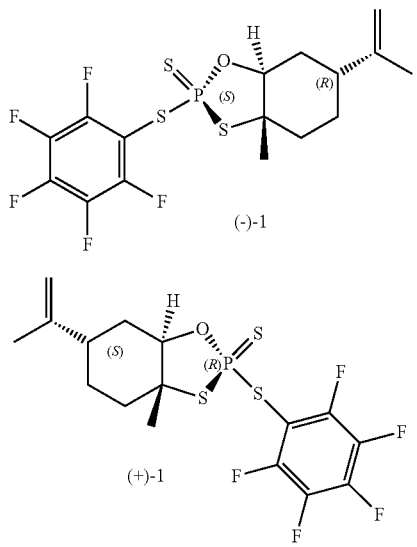

In one or all embodiments of the invention, the nucleoside of formula I has the following formula (Ia):

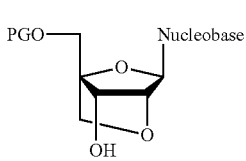

In one or all embodiments of the invention, the nucleoside of formula I has the following formula (Ib):

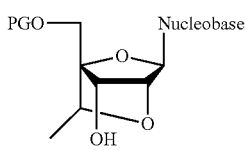

In one or all embodiments of the invention, the nucleoside of formula I has the following formula (Ic):

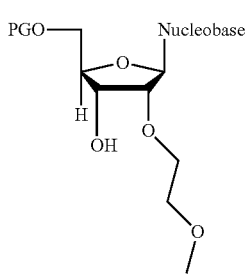

In one or all embodiments of the invention, the nucleobase is selected from the group consisting of A, T, G, C, and 5-methyl cytosine.

In one or all embodiments of the invention, the nucleobase is selected from the group consisting of A, T and G.

In one or all embodiments of the invention, the nucleobase is A, G, C or 5-methyl cytosine wherein the exocyclic amino moiety is protected by an amino protecting group. The amino protecting group can be selected from the group consisting of DMF and iBu.

In one or all embodiments, the method of the invention further comprises the step of coupling compounds of formula (IIIa) or (IIIb) as P(V) monomers for preparing an antisense oligonucleotide. This can be done according to processes known in the art.

In one or all embodiments of the invention, $R^1$ is H and $R^2$ is —O(CH$_2$)$_2$OCH$_3$.

In one or all embodiments of the invention, $R^1$ and $R^2$ together form a 2'-4' bridge selected from —CH$_2$—O— wherein the oxygen is attached via position $R^2$.

In one or all embodiments of the invention $R^1$ and $R^2$ together form a 2'-4' bridge selected from —CH(CH$_3$)O—, wherein the oxygen is attached via position $R^2$.

In one or all embodiments of the invention $R^3$ is a phenyl substituted by 1 to 5 F, for example phenyl substituted by 1, 2, 3, 4 or 5 F, for example substituted by 4 or 5 F, for example substituted by 5 F.

In one or all embodiments of the invention $R^4$ is methyl or ethyl for example methyl.

In one embodiment of the invention the method of the invention is a method for preparing a compound of formula (IIIa1) or (IIIb1) comprising the step of reacting a modified nucleoside of formula (I):

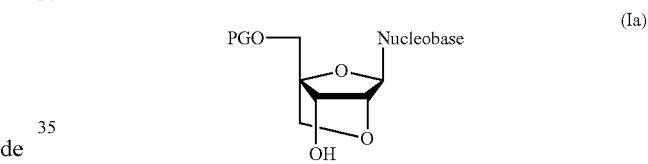

wherein PG is a hydroxyl protecting group,
with a compound of formula (IIa1) or (IIb1):

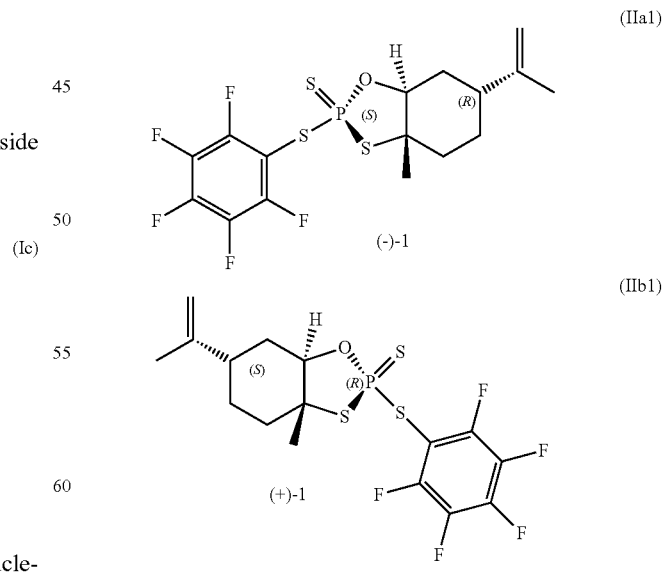

with 1,8-diazabicyclo[5.4.0]undec-7-ene (DBU) as base in MeCN, wherein DBU is used in an amount of about 0.8 equivalent to nucleoside of formula (Ia);

to produce a monomer of formula (IIIa1) or (IIIb1):

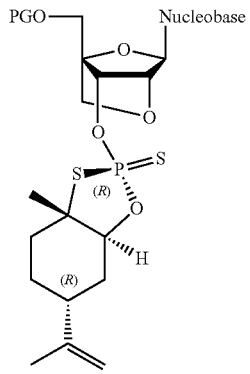
(IIIa1)

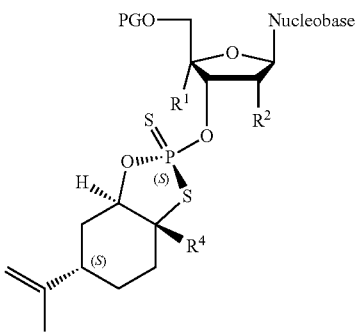
(IIIb)

wherein R¹, R², R³ and R⁴ are as defined herein.

In an embodiment, the compounds of formula (IIIa) or (IIIb) according to the invention are of formula (IIIa1) or (IIIb1):

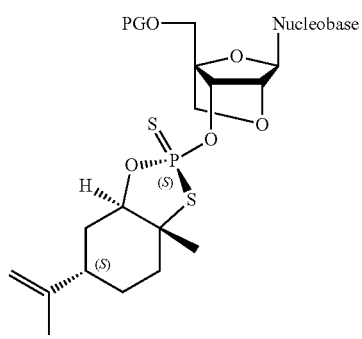
(IIIb1)

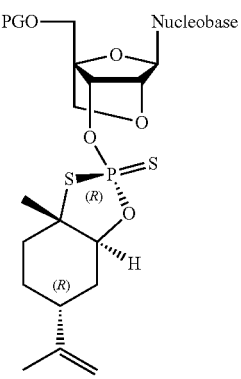
(IIIa1)

In another aspect, the invention relates to the use of 1,8-diazabicyclo[5.4.0]undec-7-ene (DBU) as base in the production of a compound of formula (IIIa) or (IIIb) starting from a nucleoside of formula (I) as described herein, wherein DBU is used in an amount of about 0.8 equivalent to nucleoside.

In another aspect, the invention relates to a compound of formula (IIIa) or (IIIb):

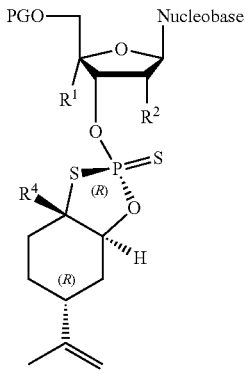
(IIIa)

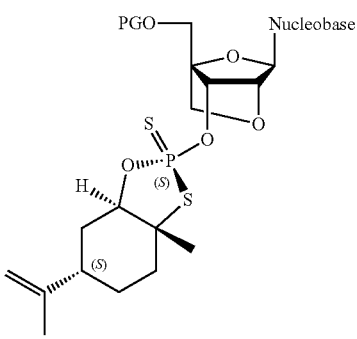
(IIIb1)

In an embodiment, the compounds of formula (IIIa) or (IIIb) according to the invention are selected from the group consisting of the following compounds:

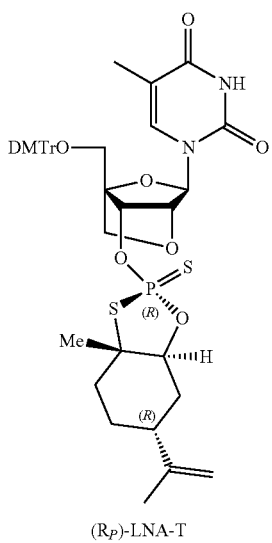
($R_P$)-LNA-T
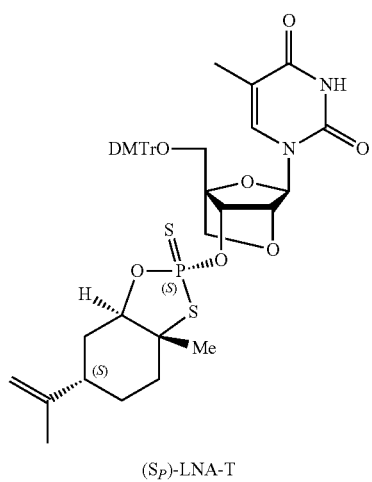
($S_P$)-LNA-T
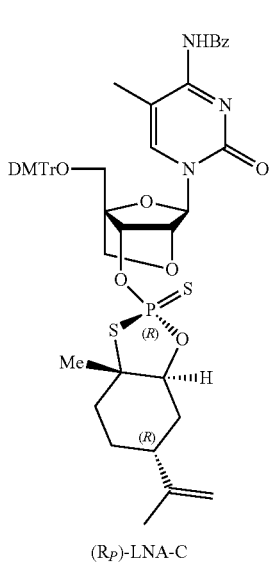
($R_P$)-LNA-C
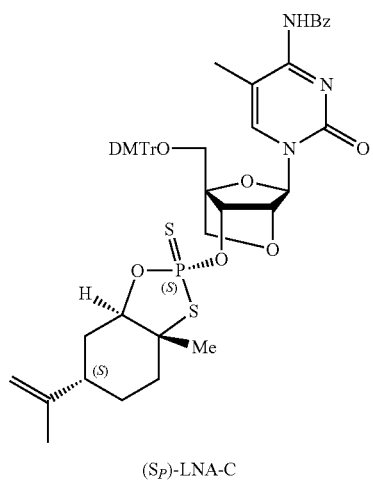
($S_P$)-LNA-C
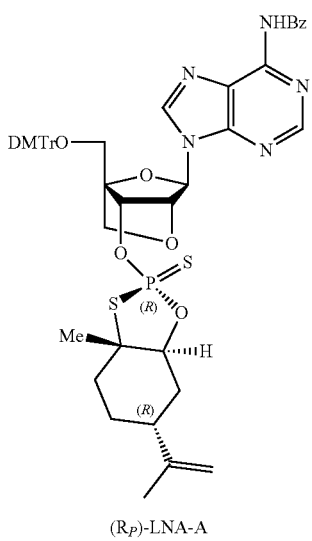
($R_P$)-LNA-A
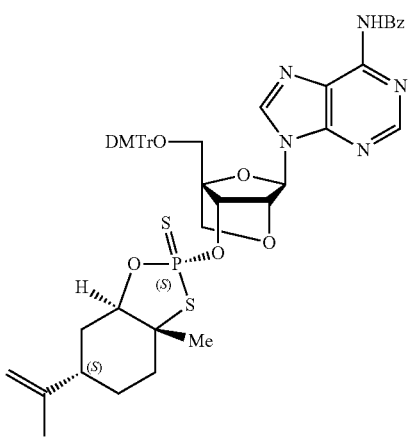
($S_P$)-LNA-A

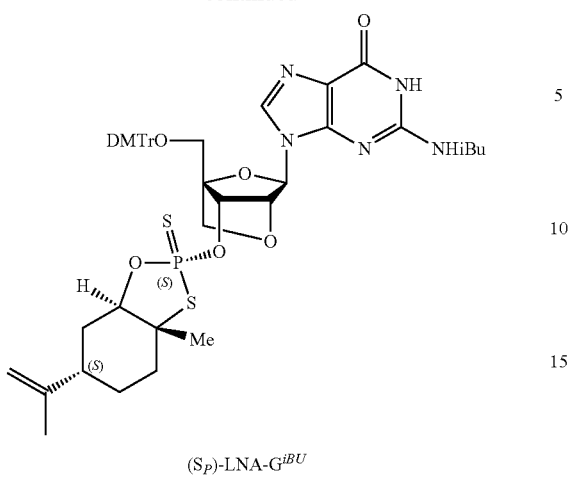
(S$_P$)-LNA-G$^{iBU}$
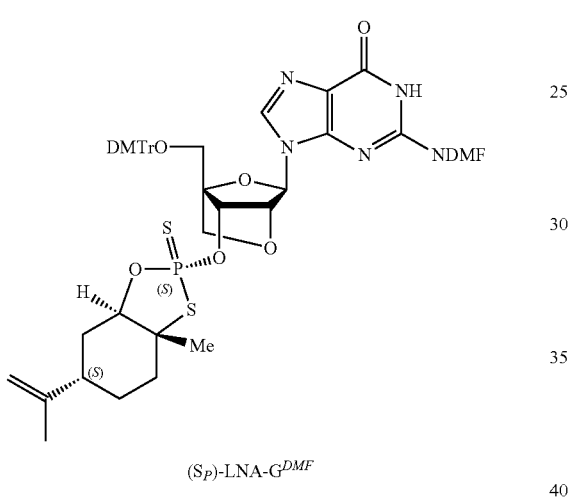
(S$_P$)-LNA-G$^{DMF}$
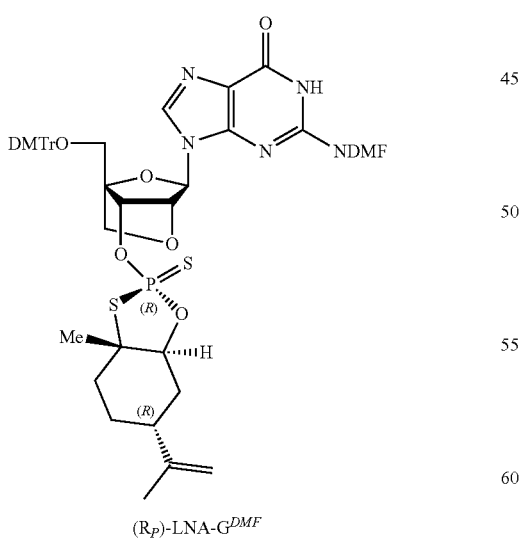
(R$_P$)-LNA-G$^{DMF}$
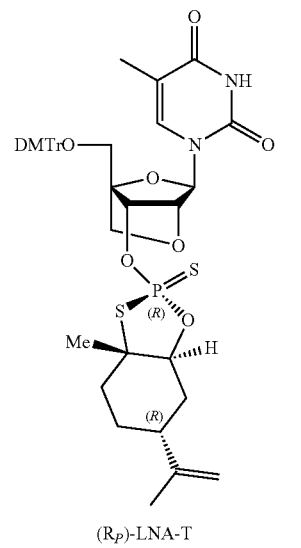
(R$_P$)-LNA-T
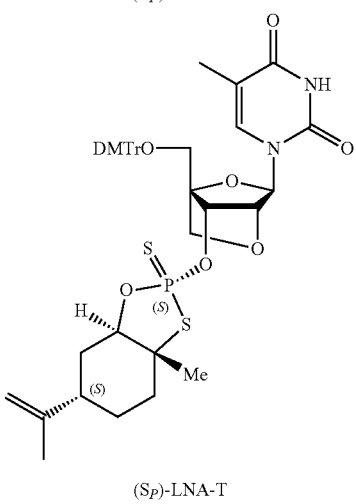
(S$_P$)-LNA-T
In an embodiment, the compounds of formula (IIIa) or (IIIb) according to the invention are the following compounds:
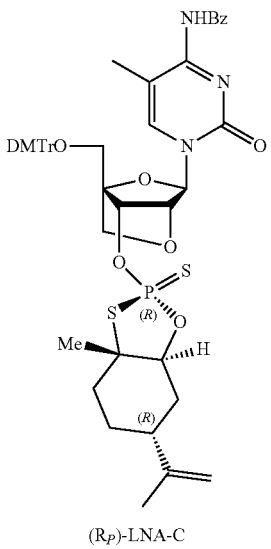
(R$_P$)-LNA-C
In an embodiment, the compounds of formula (IIIa) or (IIIb) according to the invention are the following compounds:

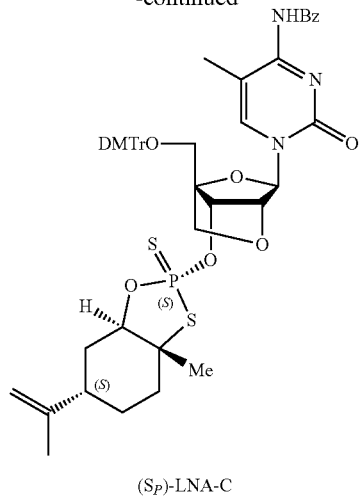
(S*P*)-LNA-C
In an embodiment, the compounds of formula (IIIa) or (IIIb) according to the invention are the following compounds:
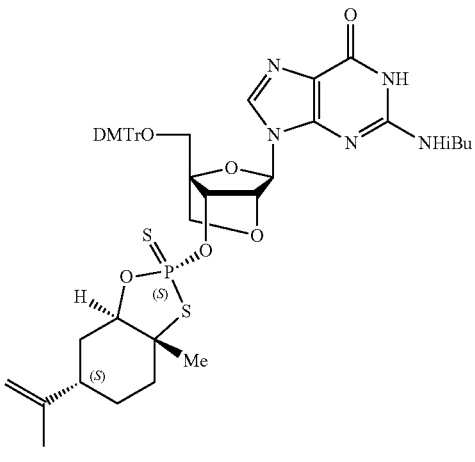
(S*P*)-LNA-G$^{iBu}$
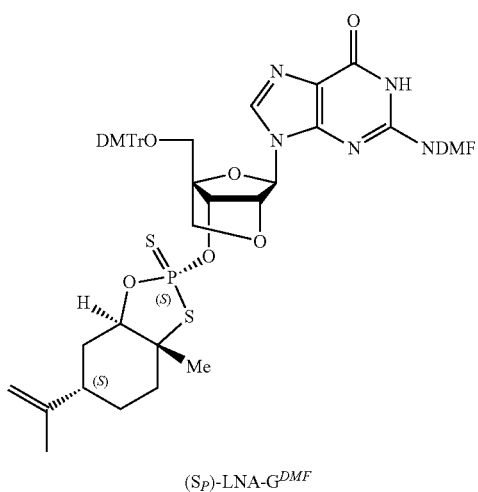
(S*P*)-LNA-G$^{DMF}$
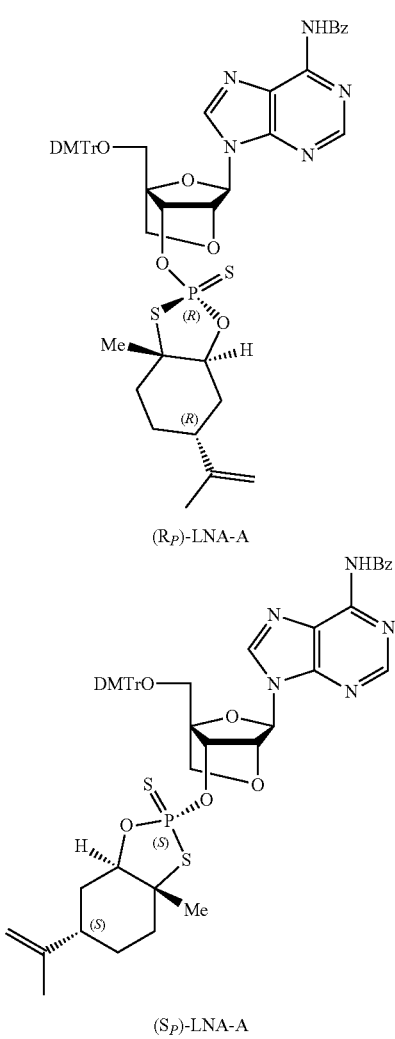
(R*P*)-LNA-A
(S*P*)-LNA-A
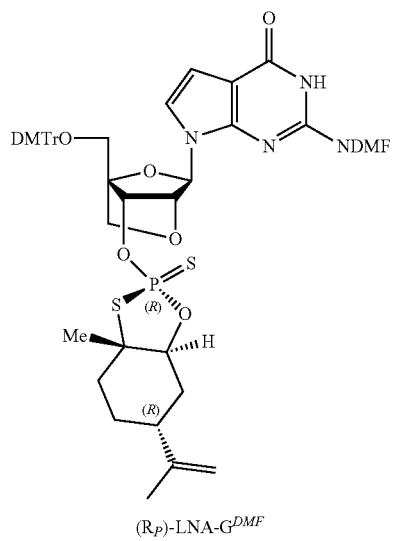
(R*P*)-LNA-G$^{DMF}$
An other aspect of the invention is a compound of formula (IIIa) or (IIIb) prepared according to the process of the invention. In one embodiment, it is a compound of formula (IIIa) or (IIIb) directly obtained by the process of the invention.

In another aspect, the invention relates to an oligonucleotide manufactured according to the method of the invention.

In one or all aspects or embodiments of the invention, DBU can be reacted in solution in MeCN. Other suitable solvents can also be contemplated by the person skilled in the art.

In one or all aspects or embodiments of the invention, the reaction can be conducted in solution in MeCN. Other suitable solvents can also be contemplated by the person skilled in the art.

In an embodiment, the compound of formula (I) is selected from the group consisting of:

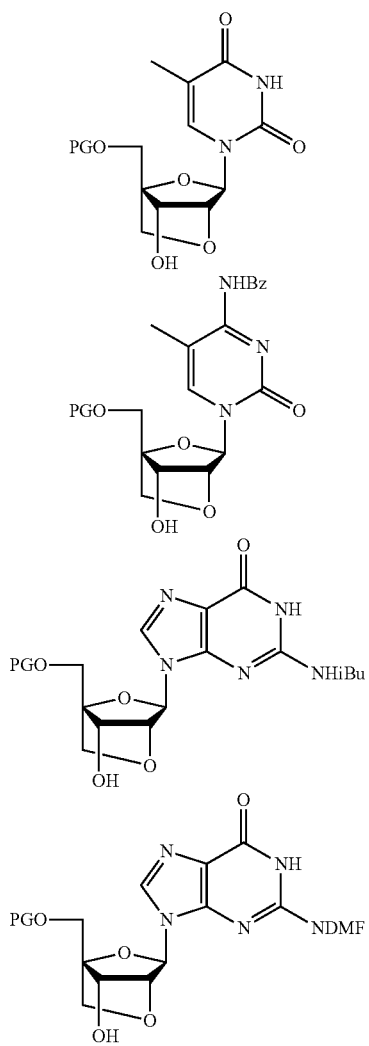

As it can be evidenced from table 6 hereinbelow, the inventors found a new process for preparing LNA monomers through a P(V) reagent based system with surprisingly optimized conditions, resulting in a cheapest and higher yield process than described in the art. For instance, when DBU is used as 0.8 equivalents in the preparation of LNA-T, LNA-A and LNA-G, the isolated yield of compounds III is significantly higher than when 1.3 DBU equivalents are used as recommended in the prior art. As for the preparation of LNA-C, the same or a better yield is obtained when using 0.8 equivalents of DBU compared to when using 1.3 DBU equivalents. This means that the process can be significantly cheaper because less DBU equivalents are needed.

EXAMPLES

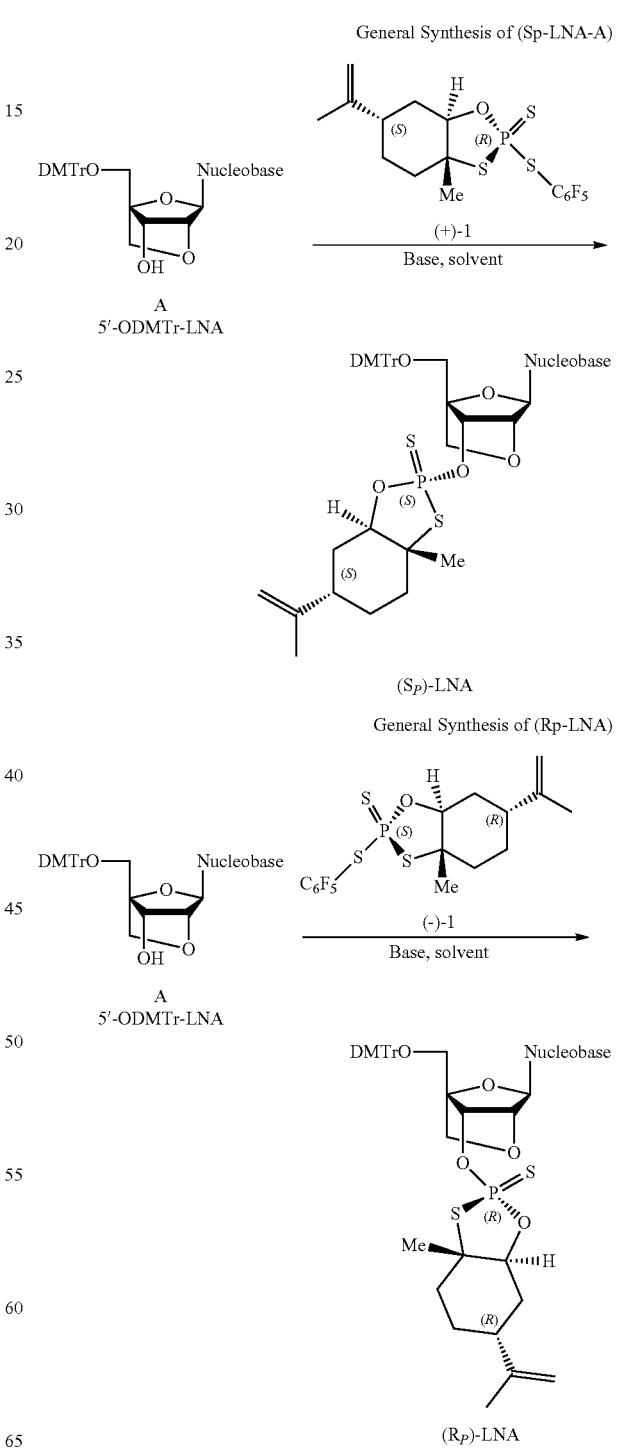

General Synthesis for P(V) LNA a Monomers Using Either 0.8 Eq DBU or 1.3 Eq DBU To suspension of 5'-ODMTr-LNA-A (500 mg 0.73 mmol) and (+)-1 (423 mg, 0.95 mmol) in MeCN (9 mL) solution of DBU (87 µL, 0.58 mmol, 0.8 eq) in MeCN (2 ml) was added at room temperature, then stirred at room temperature for 40 min (TLC-full conv.). Reaction mixture was filtered through silicagel plug, rinsed with EtOAc (35 mL). Filtrate was washed with water (15 mL) 10% $Na_2HPO_4$ (20 mL), water (20 mL), sat. $NaHCO_3$ (20 mL), dried over $Na_2SO_4$ and evaporated. Residue was purified by column chromatography (eluent EtOAc in hexanes from 50% to 70%).

TABLE 1

|  |  | Isolated yield | |
| --- | --- | --- | --- |
|  | DBU eq. | (+)-1 | (−)-1 |
| LNA-A | 0.8 | 89-91% | 80% |
|  | 1.3 | 26-65% | 76% |

General Synthesis for P(V) LNA T Monomers Using Either 0.8 Eq DBU or 1.3 Eq DBU To suspension of 5'-ODMTr-LNA-T (500 mg 0.87 mmol) and (−)-1 (507 mg 1.13 mmol) in MeCN (9 mL) solution of DBU (104 µL 0.58 mmol 0.8 eq) in MeCN (2 ml) was added at room temperature, and then stirred at room temperature for 40 min (TLC-full conv.). Reaction mixture was filtered through silicagel plug, rinsed with EtOAc (35 mL). Filtrate was washed with 10% $Na_2HPO_4$ (20 mL), water (20 mL), sat. $NaHCO_3$ (20 mL), dried over $Na_2SO_4$ and evaporated. Residue was purified by column chromatography (eluent EtOAc/hexanes+1/1).

TABLE 2

|  |  | Isolated yield | |
| --- | --- | --- | --- |
|  | DBU eq. | (+)-1 | (−)-1 |
| LNA-T | 0.8 | 83% | 88-84% |
|  | 1.3 | 62% | 79% |

General Synthesis for P(V) LNA C Monomers Using Either 0.8 Eq DBU or 1.3 Eq DBU To solution of 5'-ODMTr-LNA-C (588 mg 0.87 mmol) and (+)-1 (505 mg 1.13 mmol) in MeCN (11 mL) solution of DBU (DBU 106 µL 0.58 mmol 0.8 eq) in MeCN (2 ml) was added at room temperature, and then stirred at room temperature for 40 min (TLC-full conv.). Reaction mixture was filtered through silicagel plug, rinsed with EtOAc (35 mL). Filtrate was washed with 10% $Na_2HPO_4$ (20 mL), water (20 mL), sat. $NaHCO_3$ (20 mL), dried over $Na_2SO_4$ and evaporated. Residue was purified by column chromatography (eluent EtOAc/hexanes+1/2 then 1/1).

TABLE 3

|  |  | Isolated yield | |
| --- | --- | --- | --- |
|  | DBU eq. | (+)-1 | (−)-1 |
| LNA-C | 0.8 | 81% | 84% |
|  | 1.3 | 88% | 80% |

General Synthesis for P(V) LNA G-iBu Monomers Using Either 0.8 Eq DBU or 1.3 Eq DBU To solution of 5'-ODMTr-LNA-$G^{iBu}$ (500 mg, 0.75 mmol) and (+)-1 (434 mg, 0.97 mmol) in MeCN (11 mL) solution of DBU (91.2 µL 0.60 mmol 0.8 eq) in MeCN (1 mL) was added at room temperature, and then stirred at room temperature for 40 min (TLC-full conv.). Reaction mixture was filtered through silicagel plug, rinsed with EtOAc (35 mL). Filtrate was washed with 10% $Na_2HPO_4$ (20 mL), water (20 mL), sat. $NaHCO_3$ (20 mL), dried over $Na_2SO_4$ and evaporated. Residue was purified by column chromatography (eluent EtOAc in hexanes from 50% to 75%).

TABLE 4

|  |  | Isolated yield | |
| --- | --- | --- | --- |
|  | DBU eq. | (+)-1 | (−)-1 |
| LNA-$G^{iBu}$ | 0.8 | 79% | 83% |
|  | 1.3 | 49% | 66% |

General Synthesis for P(V) LNA G-DMF Monomers Using Either 0.8 Eq DBU or 1.3 Eq DBU To suspension of 5'-ODMTr-LNA-$G^{DMF}$ (500 mg 0.77 mmol) in MeCN (6 mL) and THF (13 mL) a solution of (+)-1 (444 mg 1.00 mmol) in MeCN (5 mL) was added, followed with solution of DBU (DBU 91.5 µL 0.61 mmol 0.8 eq) in MeCN (1 mL). The reaction mixture stirred at room temperature for 1 h (gradually LNA-$G^{DMF}$ is dissolved). Reaction mixture was filtered through silicagel plug, product was washed out from plug with EtOAc (100 mL), EtOAc/THF (1/2 80 mL), THF (50 mL). Filtrate was washed with 10% $Na_2HPO_4$ (100 mL), water (100 mL), sat. $NaHCO_3$ (100 mL), brine (100 mL) dried over $Na_2SO_4$ and evaporated. Residue was purified by column chromatography (eluent THF in EtOAc from 10% to 30%).

TABLE 5

|  |  | Isolated yield | |
| --- | --- | --- | --- |
|  | DBU eq. | (+)-1 | (−)-1 |
| LNA-$G^{DMF}$ | 0.8 | 75% | 84% |
|  | 1.3 | 43% | 54% |

TABLE 6 yield overview

|  |  | Isolated yield | |
| --- | --- | --- | --- |
|  | DBU eq. | (+)-1 | (−)-1 |
| LNA-T | 0.8 | 83% | 88-84% |
|  | 1.3 | 62% | 79% |
| LNA-C-pg | 0.8 | 81% | 84% |
|  | 1.3 | 88% | 80% |
| LNA-A-pg | 0.8 | 89-91% | 80% |
|  | 1.3 | 26-65% | 76% |
| LNA-$G^{iBu}$ | 0.8 | 79% | 83% |
|  | 1.3 | 49% | 66% |
| LNA-$G^{DMF}$ | 0.8 | 75% | 84% |
|  | 1.3 | 43% | 54% |

1.1 Analytical Data

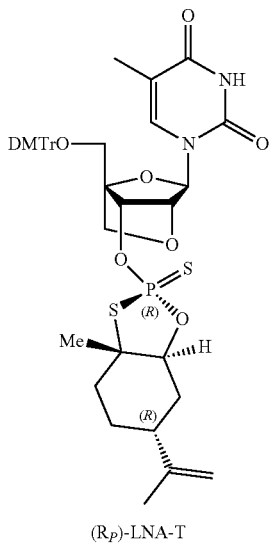

(R$_P$)-LNA-T $^1$H NMR (300 MHz, CDCl$_3$, ppm): 8.71 (1H, s), 7.64 (1H, d, J=1.2 Hz), 7.46-7.41 (2H, m), 7.36-7.26 (6H, m), 7.25-7.20 (1H, m) 6.87-7.60 (4H, m), 5.70 (1H, s), 5.16 (1H, d, J=7.3 Hz), 4.95 (1H, s), 4.85 (1H, s), 4.66 (1H, s), 4.39 (1H, dt, J=12.8 3.5 Hz), 3.81 (2H, s), 3.78 (6H, s), 3.47 (1H, d, J=11.1 Hz), 3.42 (1H, d, J=11.1 Hz), 2.60-2.52 (1H, m), 2.35-2.25 (1H, m), 2.09-1.62 (5H, m), 1.76 (3H, s), 1.67-1.64 (6H, m)

$^{13}$C NMR (100 MHz, CDCl$_3$, ppm) 163.7, 158.8, 149.9, 145.0, 144.2, 135.3, 135.2, 134.2, 130.3, 128.3, 128.2, 127.2, 113.5, 111.8, 111.0, 87.7, 87.6, 87.2, 86.9, 85.6, 78.4, 74.3, 74.2, 72.4, 66.6, 57.7, 55.4, 39.0, 33.8, 27.7, 27.6, 23.6, 22.6, 22.0, 12.7.

$^{31}$P NMR (160 MHz, CDCl$_3$, ppm) 101.4.

[α]$_D^{20}$=−37.0 (c.1, DCM).

LCMS ESI (m/z): 817.3 [M−H]$^−$

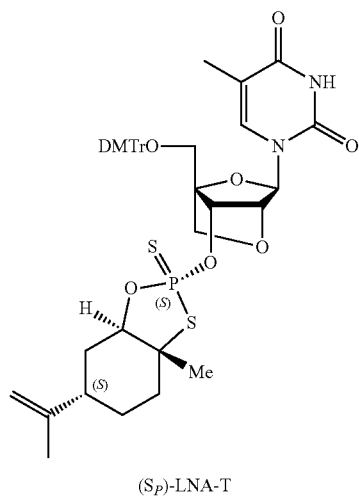

(S$_P$)-LNA-T $^1$H NMR (300 MHz, CDCl$_3$, ppm): 8.8-8.6 (1H, br. s), 7.64 (1H, d, J=1.0 Hz), 7.52-7.46 (2H, m), 7.40-7.33 (4H, m), 7.33-7.26 (2H, m), 7.26-7.19 (1H, m) 6.87-7.79 (4H, m), 5.69 (1H, s), 5.25 (1H, d, J=11.0 Hz), 4.90-4.88 (1H, m), 4.57 (1H, s), 4.60 (1H, s), 4.29 (1H, dt, J=12.6 3.1 Hz), 3.87 (1H, d, J=8.3 Hz), 3.79-3.76 (1H, m), 3.78 (3H, s), 3.78 (3H, s), 3.59 (1H, d, J=11.0 Hz), 3.42 (1H, d, J=11.0 Hz), 2.57-2.48 (1H, m), 2.08-1.65 (6H, m), 1.65 (6H, s), 1.58 (3H, d, J=1.0 Hz)

$^{13}$C NMR (100 MHz, CDCl$_3$, ppm): 163.7, 158.8, 149.9, 144.9, 144.2, 135.3, 135.2, 134.2, 130.5, 130.4, 128.5, 128.1, 127.2, 113.4, 113.4, 111.9, 111.1, 87.4, 87.1, 86.1, 78.3, 78.3, 74.6, 74.6, 72.2, 65.9, 57.9, 55.3, 39.0, 33.8, 33.7, 27.8, 27.6, 23.5, 22.7, 21.8, 12.6.

$^{31}$P NMR (160 MHz, CDCl$_3$, ppm): 100.9.

[α]$_D^{20}$=+94.9 (c. 1, DCM).

LCMS ESI (m/z): 817.25 [M−H]$^−$

(R$_P$)-LNA-C $^1$H NMR (300 MHz, CDCl$_3$, ppm): 13.5-13.2 (1H, br. s), 8.35-8.28 (2H, m), 7.82 (1H, J=1.0 Hz), 7.55-7.40 (5H, m), 7.39-7.28 (6H, m), 7.27-7.22 (1H, m), 6.86-6.83 (4H, m), 5.75 (1H, s), 5.19 (1H, d, J=7.5 Hz), 4.95 (1H, s), 4.86 (1H, s), 4.71 (1H, s), 4.40 (1H, dt, J=12.7, 3.5 Hz), 3.84-3.79 (7H, m), 3.50 (1H, d, J=11.1 Hz), 3.44 (1H, d, J=11.1 Hz), 2.62-2.52 (1H, m), 2.36-2.25 (1H, m), 2.09-1.66 (6H, m), 1.85 (3H, d, J=1.0 Hz), 1.76 (3H, s), 1.65 (3H, s).

$^{13}$C NMR (100 MHz, CDCl$_3$, ppm): 159.8, 158.8, 147.7, 145.0, 144.2, 137.3, 135.4, 135.3, 135.2, 132.6, 130.3, 130.1, 128.3, 128.4, 127.2, 113.5, 112.2, 111.8, 87.9, 87.8, 87.5, 87.6, 85.6, 78.3, 74.1, 74.0, 72.4, 66.7, 57.7, 55.4, 39.0, 33.8, 33.7, 27.7, 27.6, 23.6, 22.7, 22.0, 13.8.

$^{31}$P NMR (160 MHz, CDCl$_3$, ppm) 101.4

[α]$_D^{20}$=+15.9 (c 0.1, DCM).

LCMS ESI (m/z: ): 922.81 [M+H]$^+$

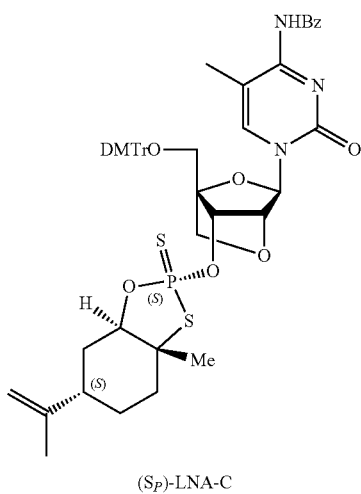

(S*P*)-LNA-C

¹H NMR (300 MHz, CDCl₃, ppm): 13.5-13.3 (1H, br. s), 8.33-8.28 (2H, m), 7.82 (1H, d, J=1.0 Hz), 7.55-7.48 (3H, m), 7.46-7.37 (6H, m), 7.35-7.29 (2H, m), 7.27-7.22 (1H, m), 6.89-6.81 (4H, m), 5.74 (1H, s), 5.28 (1H, d, J=11.2 Hz), 4.92-4.88 (1H, m), 4.86 (1H, s), 4.65 (1H, s), 4.30 (1H, dt, J=12.7, 3.2 Hz), 3.89 (1H, d, J=8.2 Hz), 3.81-3.77 (1H, m), 3.79 (3H, s), 3.79 (3H, s), 3.62 (1H, d, J=11.0 Hz), 3.44 (1H, d, J=11.0 Hz), 2.57-2.48 (1H, m), 2.08-1.62 (6H, m), 1.78 (3H, d, J=1.0 Hz), 1.66 (3H, s), 1.65 (3H, s)

¹³C NMR (100 MHz, CDCl₃, ppm): 159.8, 158.9, 158.8, 147.7, 144.9, 144.2, 137.2, 135.4, 135.3, 135.2, 132.6, 130.5, 130.1, 128.5, 128.3, 128.2, 127.2, 113.4, 113.4, 112.2, 111.9, 87.6, 87.5, 87.4, 87.1, 86.1, 78.2, 78.1, 74.5, 74.4, 72.3, 65.9, 57.9, 55.4, 38.9, 33.8, 33.7, 27.8, 27.6, 23.5, 22.7, 21.8, 13.7.

³¹P NMR (160 MHz, CDCl₃, ppm): 100.9.

[α]_D²⁰=+152.3 (c. 1, DCM).

LCMS ESI (m/z): 922.79 [M+H]⁺

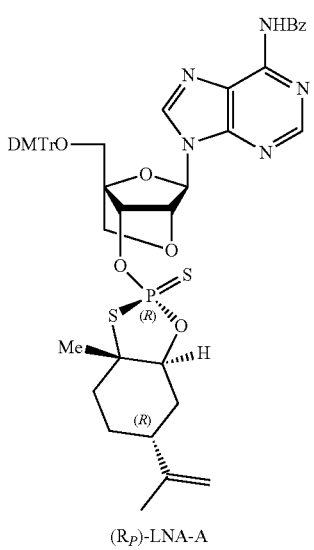

(R*P*)-LNA-A

¹H NMR (300 MHz, CDCl₃, ppm): 9.04 (1H, s), 8.82 (1H, s), 8.38 (1H, s), 8.06-7.97 (2H, m), 7.63-7.55 (1H, m), 7.55-7.47 (2H, m), 7.46-7.39 (2H, m), 7.36-7.25 (1H, m), 7.24-7.17 (1H, m) 6.88-6.78 (4H, m), 6.22 (1H, s), 5.32 (1H, d, J 6.75 Hz), 4.98 (1H, s), 4.96 (1H, s), 4.88 (1H, s), 4.42 (1H, dt, J=12.7 3.5 Hz), 4.05 (1H, d, J 8.4 Hz), 3.96 (1H, d, J=8.4 Hz), 3.78 (6H, s), 3.49 (2H, s), 2.62-2.53 (1H, m), 2.35-1.2.25 (1H, m), 2.11-1.64 (5H, m), 1.78 (3H, s), 1.63 (3H, s)

¹³C NMR (100 MHz, CDCl₃, ppm): 164.6, 158.7, 153.2, 151.2, 149.7, 145.0, 144.3, 140.2, 135.4, 135.3, 133.7, 132.9, 130.2, 129.0, 128.2, 128.1, 128.0, 127.1, 123.4, 113.4, 111.8, 87.5, 87.4, 86.7, 85.9, 85.6, 78.7, 75.7, 75.6, 73.0, 66.6, 58.5, 55.4, 39.0, 33.8, 33.7, 27.7, 27.6, 23.5, 22.6, 22.0.

³¹P NMR (160 MHz, CDCl₃, ppm) 101.6.

[α]_D²⁰=−71.7 (c. 1, DCM).

LCMS ESI (m/z): 932.7 [M+H]⁺

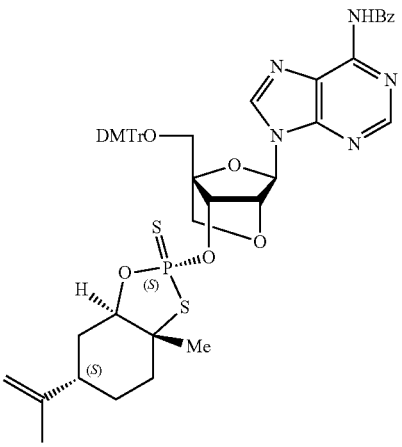

(S*P*)-LNA-A

¹H NMR (300 MHz, CDCl₃, ppm): 9.1-9.0 (1H, br, s), 8.80 (1H, s), 8.33 (1H, s), 8.04-7.98 (2H, m), 7.62-7.56 (1H, m) 7.54-7.43 (4H, m), 7.37-7.26 (6H, m), 7.24-7.18 (1H, m) 6.85-6.80 (4H, m), 6.20 (1H, s), 5.42 (1H, d, J=10.4 Hz), 4.95 (1H, s), 4.84 (1H, s), 4.66 (1H, s), 4.31 (1H, dt, J=12.6 3.3 Hz), 4.14 (1H, d, J=8.4 Hz), 3.95 (1H, d, J=8.4 Hz), 3.77 (6H, s), 3.59 (1H, d, J=11.0 Hz), 3.53 (1H, d, J=11.0 Hz), 2.56-2.47 (1H, m), 2.10-1.60 (6H, m), 1.64-1.60 (6H, m).

¹³C NMR (100 MHz, CDCl₃, ppm): 164.6, 158.7, 153.0, 151.0, 149.6, 144.8, 144.2, 140.3, 135.4, 135.3, 133.6, 132.9, 130.2, 129.9, 128.2, 128.0, 127.9, 127.0, 123.4, 113.3, 111.8, 87.2, 87.1, 86.7, 86.1, 85.9, 78.6, 78.5, 76.0, 75.9, 72.8, 65.8, 58.9, 55.2, 38.0, 33.6, 33.6, 27.6, 27.5, 23.3, 22.5, 21.6.

³¹P NMR (160 MHz, CDCl₃, ppm): 101.1.

[α]_D²⁰=+48.5 (c 0.1, DCM).

LCMS ESI (m/z): 932.7 [M+H]⁺

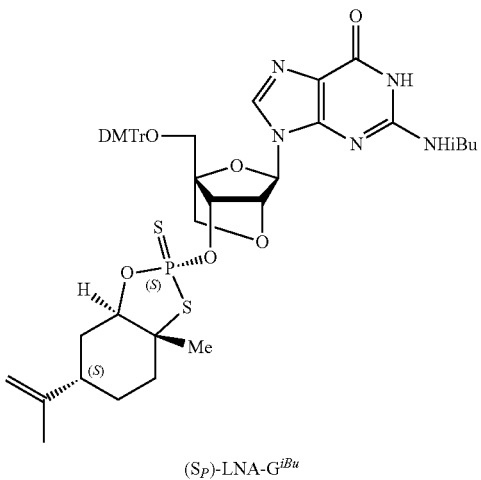

($S_P$)-LNA-G$^{iBu}$

¹H NMR (400 MHz, CDCl₃, ppm): 12.02 (1H, s), 8.97 (1H, s), 7.79 (1H, s), 7.44-7.38 (2H, m), 7.34-7.23 (6H, m), 7.22-7.17 (1H, m), 6.84-6.77 (4H, m), 5.99 (1H, d, J=10.3 Hz), 5.83 (1H, s), 4.97 (1H, s), 4.91-4.88 (1H, m), 4.73 (1H, s), 4.40 (1H, dt, J=12.6, 3.2 Hz), 4.15 (1H, d, J=8.7 Hz), 3.95 (1H, d, J=8.7 Hz), 3.78 (3H, s), 3.78 (3H, s), 3.55-3.49 (2H, m), 2.64 (1H, septet, J=6.8 Hz), 2.60-2.53 (1H, m), 2.20-2.11 (1H, m), 2.10-1.65 (5H, m), 1.70 (3H, s), 1.69 (3H, s), 1.27 (3H, d, J=6.8 Hz), 1.25 (3H, d, J=6.8 Hz).

¹³C NMR (100 MHz, CDCl₃, ppm): 178.7, 158.7, 155.5, 147.5, 147.2, 144.8, 144.4, 138.6, 135.4, 130.3, 128.3, 128.0, 127.0, 122.3, 113.30, 111.9, 87.1, 87.0, 86.6, 86.5, 78.4, 73.0, 66.5, 59.3, 55.3, 38.9, 36.7, 33.9, 33.8, 27.8, 27.7, 23.5, 22.7, 21.8, 19.2, 19.0.

³¹P NMR (160 MHz, CDCl₃, ppm): 100.3.

$[\alpha]_D^{20}$=+85.3 (c 0.1, DCM).

LCMS ESI (m/z): 914.73 [M+H]⁺

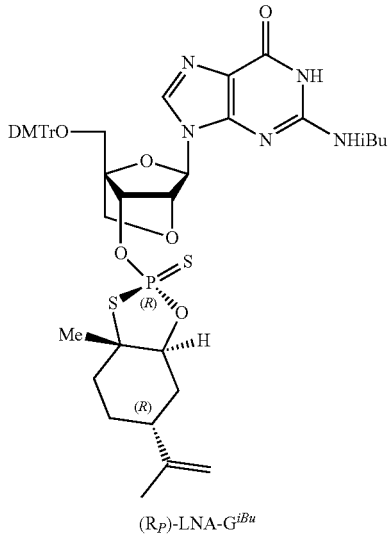

($R_P$)-LNA-G$^{iBu}$

¹H NMR (400 MHz, CDCl₃, ppm): 11.99 (1H, s), 8.89 (1H, s), 7.81 (1H, s), 7.43-7.37 (2H, m), 7.33-7.23 (6H, m), 7.22-7.17 (1H, m), 6.84-6.78 (4H, m), 5.97 (1H, J=7.7 Hz), 5.84 (1H, s), 5.01-4.87 (1H, m), 4.93-4.87 (2H, m), 4.51 (1H, dt, J=12.7 3.5 Hz), 4.07 (1H, J=8.5 Hz), 4.00 (1H, J=68.5 Hz), 3.78 (6H, s), 3.48-3.41 (2H, m), 2.63-2.56 (1H, m), 2.57 (1H, septet, J=6.9 Hz), 2.36-2.25 (1H, m), 2.14-1.64 (5H, m), 1.78 (3H, s), 1.68 (3H, s), 1.24 (3H, d, J=6.9 Hz), 1.22 (3H, d, J=6.9 Hz).

¹³C NMR (100 MHz, CDCl₃, ppm): 178.5, 158.7, 155.5, 147.5, 147.3, 144.8, 144.4, 138.5, 135.4, 130.2, 128.2, 128.0, 127.0, 122.2, 113.3, 111.9, 87.2, 87.1, 86.6, 86.5, 86.1, 79.2, 73.0, 66.6, 58.9, 55.3, 39.0, 36.6, 33.7, 33.6, 27.9, 27.8, 23.5, 22.7, 22.0, 19.1, 18.9.

³¹P NMR (160 MHz, CDCl₃, ppm): 103.3.

$[\alpha]_D^{20}$=−14.6 (c. 1, DCM).

LCMS ESI (m/z): 914.77 [M+H]⁺

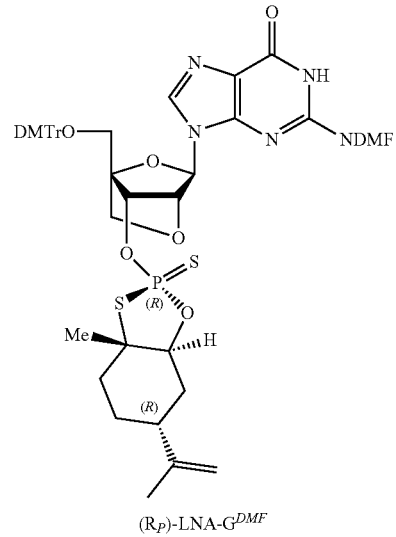

($R_P$)-LNA-G$^{DMF}$

¹H NMR (400 MHz, CDCl₃, ppm): 9.2-9.0 (1H, br. s), 8.59 (1H, s), 8.0-7.8 (1H, br. s), 7.44-7.39 (2H, m), 7.34-7.23 (6H, m), 7.22-7.16 (1H, m), 6.75-6.77 (4H, m), 5.97 (1H, s), 5.39 (1H, d, J=6.5 Hz), 4.98-4.92 (2H, m), 4.88-4.85 (1H, m), 4.41 (1H, dt, J=12.5 3.5 Hz), 4.03 (1H, d, J=8.2 Hz), 3.93 (1H, d, J=8.2 Hz), 3.77 (6H, s), 3.51 (1H, d, J=10.9 Hz), 3.43 (1H, d, J=10.9 Hz), 3.10 (3H, s), 3.05 (3H, s), 2.59-2.52 (1H, m), 2.32-2.22 (1H, m), 2.07-1.65 (5H, m), 1.76 (3H, s), 1.62 (3H, s).

¹³C NMR (100 MHz, CDCl₃, ppm): 158.7, 158.5, 157.1, 149.6, 145.1, 144.3, 135.5, 135.4, 130.2, 128.3, 128.1, 127.0, 113.4, 111.8, 87.1, 87.1, 86.6, 86.1, 85.7, 79.1, 75.9, 75.8, 73.0, 66.3, 58.8, 55.4, 41.4, 39.0, 35.3, 33.8, 33.7, 27.8, 27.6, 23.5, 22.7, 21.9, 21.3.

³¹P NMR (160 MHz, CDCl₃, ppm): 100.6.

$[\alpha]_D^{20}$=−37.4 (c. 1, THF).

LCMS ESI (m/z): 899.71 [M+H]⁺

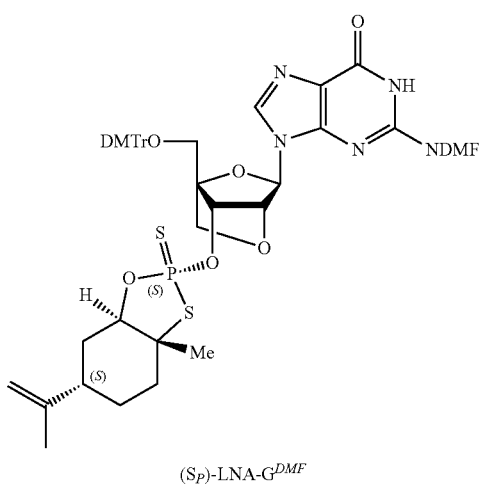

(S*p*)-LNA-G$^{DMF}$ $^1$H NMR (400 MHz, CDCl$_3$, ppm): 9.2-9.0 (1H, br. s), 8.55 (1H, s), 8.0-7.8 (1H, br. s), 7.48-7.41 (2H, m), 7.37-7.34 (6H, m), 7.22-7.16 (1H, m), 6.84-6.74 (4H, m), 5.96 (1H, s), 5.39 (1H, d, J=9.5 Hz), 4.96-4.75 (2H, m), 4.85-4.81 (1H, m), 4.27 (1H, dt, J=12.7 3.1 Hz), 4.14 (1H, d, J=8.3 Hz), 3.92 (1H, d, J=8.3 Hz), 3.76 (6H, s), 3.64-3.50 (2H, m), 3.12 (3H, s), 3.06 (3H, s), 2.55-2.46 (1H, m), 2.09-1.58 (6H, m), 1.53 (3H, s), 1.61 (3H, s).

$^{13}$C NMR (100 MHz, CDCl$_3$, ppm): 158.7, 158.3, 157.0, 144.9, 144.4, 135.5, 135.4, 130.3, 130.2, 128.3, 128.1, 127.5, 127.1, 113.4, 113.4, 111.8, 87.0, 86.7, 86.2, 79.0, 76.3, 76.2, 73.0, 65.8, 59.4, 55.3, 41.5, 38.9, 35.3, 33.7, 33.7, 27.7, 27.5, 23.4, 22.6, 21.7.

$^{31}$P NMR (160 MHz, CDCl$_3$, ppm): 100.0.

[α]$_D^{20}$=+70.8 (c 0.1, THF).

LCMS ESI (m/z): 899.74 [M+H]$^+$

The invention claimed is:

1. A method for preparing a compound of formula (IIIa) or (IIIb) comprising the step of reacting a modified nucleoside of formula (I):

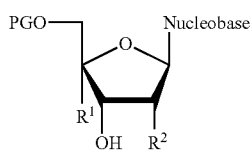

wherein PG is a hydroxyl protecting group,
R$^1$ is H and R$^2$ is —O(CH$_2$)$_2$OCH$_3$ or,
R$^1$ and R$^2$ together form a 2'-4' bridge selected from —CH$_2$-O- or —CH(CH$_3$)O—, wherein the oxygen is attached via position R$^2$;
with a compound of formula (IIa) or (IIb):

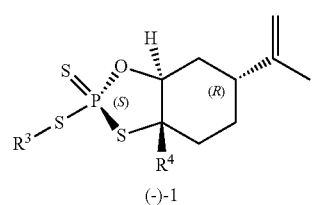

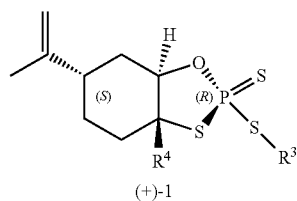

wherein R$^3$ is a C$_6$-C$_{10}$ aryl substituted by halo and halo is selected from F, Cl and Br and R$^4$ is a linear or branched C$_1$-C$_6$-alkyl;
with 1,8-diazabicyclo [5.4.0] undec-7-ene (DBU) as base, wherein DBU is used in an amount of about 0.8 equivalent to nucleoside of formula (I);
to produce a monomer of formula (IIIa) or (IIIb):

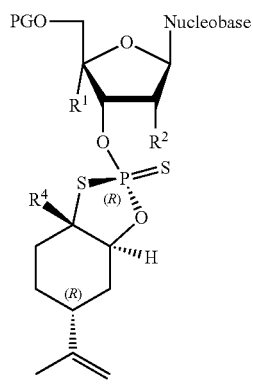

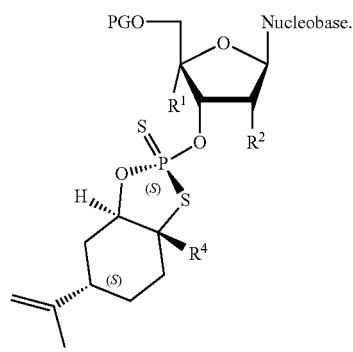

2. The method of claim 1, wherein the nucleoside of formula I has the following formula (Ia):

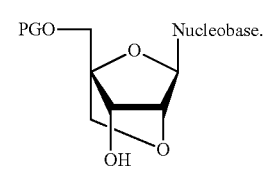

3. The method of claim 1, wherein the nucleoside of formula I has the following formula (Ib):

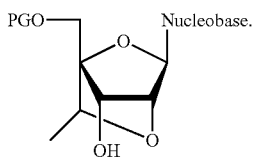

(Ib)

4. The method of claim 1, wherein the nucleoside of formula I has the following formula (Ic):

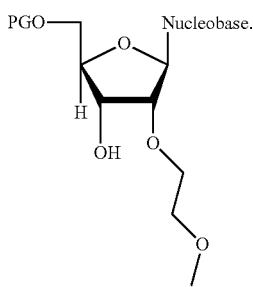

(Ic)

5. The method of claim 1 wherein the nucleobase is selected from the group consisting of A, T, G, C, and 5-methyl cytosine.

6. The method of claim 1 wherein the nucleobase is selected from the group consisting of A, T and G.

7. The method of claim 5 wherein in A, G, C or 5-methyl cytosine the exocyclic amino moiety is protected by an amino protecting group.

8. The method of claim 7, wherein the amino protecting group is selected from the group consisting of DMF or iBu.

9. The method of claim 1 further comprising the step of coupling compounds of formula (IIIa) or (IIIb) as P(V) monomers for preparing an antisense oligonucleotide.

10. The method of claim 1, wherein $R^1$ is H and $R^2$ is —O$(CH_2)_2OCH_3$.

11. The method of claim 1, wherein $R^1$ and $R^2$ together form a 2'-4' bridge selected from —$CH_2$—O— wherein the oxygen is attached via position $R^2$.

12. The method of claim 1, wherein $R^1$ and $R^2$ together form a 2'-4' bridge selected from —CH($CH_3$)O—, wherein the oxygen is attached via position $R^2$.

13. The method of claim 1, wherein $R^3$ is a phenyl substituted by 1 to 5 F.

14. The method of claim 1, wherein $R^4$ is methyl or ethyl.

* * * * *